United States Patent [19]

Warriner

[11] Patent Number: Plant 6,971

[45] Date of Patent: Aug. 8, 1989

[54] ROSE PLANT JACSTOP

[75] Inventor: William A. Warriner, Tustin, Calif.

[73] Assignee: Jackson & Perkins Company, Medford, Oreg.

[21] Appl. No.: 228,398

[22] Filed: Aug. 4, 1988

[51] Int. Cl.[4] ..... A01H 5/00

[52] U.S. Cl. ..... Plt./20

[58] Field of Search ..... Plt. 20

*Primary Examiner*—James R. Feyrer

*Attorney, Agent, or Firm*—Majestic, Parsons, Siebert & Hsue

[57] ABSTRACT

A rose variety of the hybrid tea class is provided that has a high production of attractive red color flowers with a long vase life that are produced over a short flower cycle. Blooms are borne on long straight stems and the plant has reduced thorniness, sparse foliage, and is resistant to powdery mildew.

1 Drawing Sheet

SUMMARY OF THE INVENTION

The present invention related to a new and distinct variety of rose plant of the hybrid tea class, which was originated by me by crossing the variety Jacshow, U.S. Plant Pat. No. 4,851, with an unnamed seedling.

The primary objective of this breeding was to produce a new rose variety of the hybrid tea class displaying bright red flower color and having the mildew resistance of the Jacshow variety along with the vigor and high yield of the unnamed seedling. This objective was substantially achieved, along with other desirable improvements, as evidenced by the following unique combination of characteristics which are outstanding in the new variety and which distinguish it from its parents as well as from all other varieties of which I am aware. For example, this new rose variety has:

1. High production;
2. A short cycle time;
3. Long straight stems;
4. Reduced thorniness;
5. Resistance to powdery mildew;
6. Sparse foliage;
7. A long vase life; and
8. An attractive red flower color.

Asexual reproduction of this new variety by budding, as performed at Wasco, Calif., shows that the foregoing characteristics and distinctions come true to form and are established and transmitted through succeeding propagation.

DESCRIPTION OF THE DRAWING

The accompanying illustration shows typical specimens of the vegetative growth and flowers of this new variety in different stages of development, depicted in color as nearly true as it is reasonably possible to make the same in a color illustration of this character.

DETAILED DESCRIPTION OF THE INVENTION

The following is a detailed description of my new rose variety, which has been denominated "Jacstop". Color terminology is in accordance with The Royal Horticultural Society Colour Chart except where an ordinary dictionary significant for the color is apparent.

Observations of the buds and flowers were made from specimens grown in a garden at Irvine, Calif.

Flower

The blooming habit is recurrent. The bud size is one and one-half to two inches when the petals start to unfurl. The bud form is pointed ovoid. The bud color when sepals first divide is near Red Group 44A. When half blown, the upper side of petals is near Red Group 44A. The lower side of petals is near Red Group 44A. The sepals have a color near Green Group 138B. The surface texture is covered with fine hairs. There are three normally appendaged sepals, and two unappendaged sepals with a hairy edge. The receptacle color is near Green Group 138B, has a funnel shape, small size and smooth surface. The peduncle is long and has a smooth surface with an occasional gland. Peduncle color is medium green and the peduncle is stiff and erect.

Bloom

Bloom size is large, with an average open size of four to four and one half inches, born singly. The stems are strong and long in length. The form when first open is high center and is retained to the end. The outer petals curl back quill fashion. Unlike the Jacshow variety, with 20 to 25 petals, under normal conditions there are 35 to 40 petals. The upper side and the reverse side of the petals at the flower center are both near Red Group 44A. The base of petals has a small greenish yellow half moon at the point of attachment to the receptacle. The major color is near Red Group 44A. There are no variegations except for an occasional whitish green streak on the guard petals. The general tonality at the end of the first day shows no change in color. At the end of the third day, there is still no change in color.

There is no fragrance. The petal texture is thick. The petal shape is round with a small point. The petal form has slightly recurved tips and slightly quilled edges.

The arrangement is imbricated with no pentaloids in the center. The blooms drop off cleanly, and last both on the plant and as a cut flower for a very long time.

This rose plant variety has a short cycle time between production cuts. It averages five to ten days faster than other red hybrid tea varieties presently used for cut flower production.

Reproductive Parts

There are a medium number of anthers of reddish yellow color and arranged regularly around the styles.

The filaments are white, the pollen is lemon yellow, the styles are white, and the stigmas are red.

Plant

The plant has very vigorous, upright growth of bush form.

Foliage

The foliage is medium size and sparse in quantity. New foliage is reddish colored and old foliage is dark green. A normal mid-stem leave has five leaflets.

The leaflets have an oval pointed shape, are smooth textured, and have a serrated edge. The serration is single and medium. Petiole rachis is reddish, and petiole underside is smooth, with occasional prickles. Stipules are medium and serrated with glands. The foliage is resistant to mildew under normal growing conditions at Irvine, Calif.

Wood

New wood is reddish colored with a smooth bark. Old wood is green with a smooth bark.

Prickles

There are few prickles on the main canes from the base and on the laterals from the main canes, in contrast to the Jacshow variety parent with an ordinary number of prickles. The prickles are short and hooked downward. The prickles are red colored when young. There are no small prickles on the main stalks or laterals.

Parentage

The seed parent was of the variety Jacshow. The pollen parent was an unnamed seedling.

Classification

Botanical is rosa hybrid. Commercial is hybrid tea.

I claim:

1. A new and distinct variety of rose plant of the hybrid tea class substantially as herein shown and described, characterized particularly as to novelty by clear red flower color with 35 to 40 petals, resistance to powdery mildew, long straight stems, high cut flower production, sparse foliage, short time between flower cycles, reduced thorniness and long vase life.

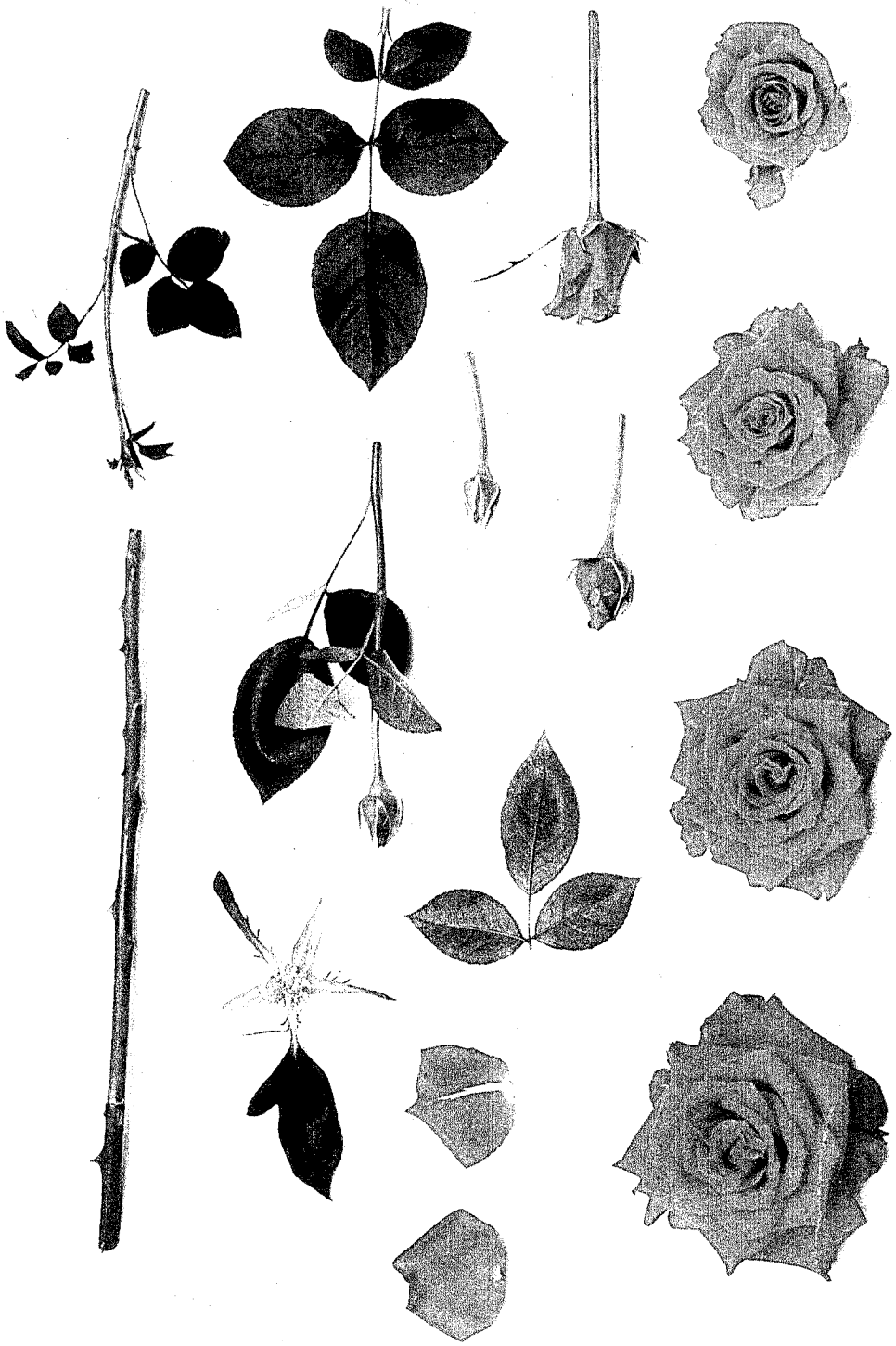

* * * * *